United States Patent [19]

Machida et al.

[11] 4,285,940
[45] Aug. 25, 1981

[54] CEPHALOSPORIN DERIVATIVES, AND ANTIBACTERIAL DRUGS COMPRISING SAID DERIVATIVES

[75] Inventors: Yoshimasa Machida, Wako; Isao Saito, Chofu; Seiichiro Nomoto, Tokyo; Shigeto Negi, Kodaira; Hironori Ikuta, Tokyo; Kyosuke Kitoh, Kawagoe, all of Japan

[73] Assignee: Eisai Co., Ltd., Tokyo, Japan

[21] Appl. No.: 137,754

[22] Filed: Apr. 7, 1980

[30] Foreign Application Priority Data

Nov. 19, 1979 [JP] Japan .................... 54-148834

[51] Int. Cl.$^3$ .......................................... C07D 501/26
[52] U.S. Cl. ...................................... 424/246; 544/28
[58] Field of Search ................. 544/28, 30, 27, 26, 544/21; 424/246

[56] References Cited

U.S. PATENT DOCUMENTS 4,015,000  3/1977  Kocsis et al. .................. 544/27

*Primary Examiner*—Nicholas S. Rizzo
*Attorney, Agent, or Firm*—Wenderoth, Lind & Ponack

[57] ABSTRACT

New cephalosporin derivatives having the general formula:

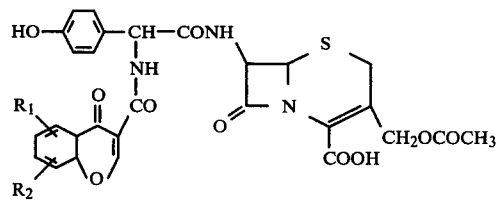

wherein $R_1$ and $R_2$ each represents hydroxy or acyloxy and their salts, and processes for the production thereof. The cephalosporin derivatives of the present invention are useful as antibacterial drugs.

7 Claims, No Drawings

CEPHALOSPORIN DERIVATIVES, AND ANTIBACTERIAL DRUGS COMPRISING SAID DERIVATIVES

This invention relates to new cephalosporin derivatives having the general formula (I):

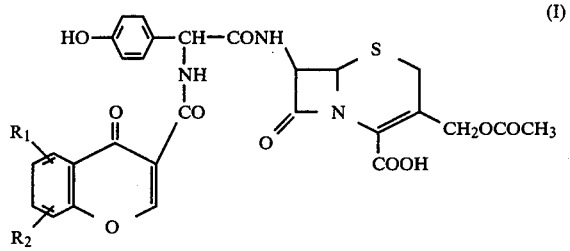

wherein $R_1$ and $R_2$ each represents hydroxy or acyloxy or their salts, processes for the production thereof and antibacterial drugs comprising them.

Illustrative of acyloxy represented as $R_1$ and $R_2$ in the above formula (I) are acetoxy, propionyloxy, benzoyloxy, etc. Also, the illustrative salts of the compounds having the general formula (I) include sodium salts, potassium salts, calcium salts, ammonium salts, triethylamine salts, dicyclohexylamine salts, procaine salts, etc.

The compound represented by the formula (II):

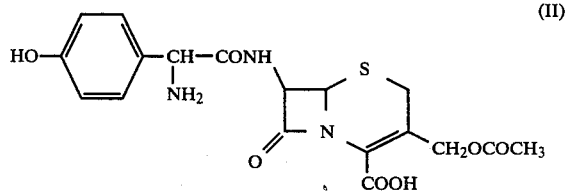

is disclosed in British Pat. No. 1,240,687 (1971) as an antibiotic.

The compounds of the present invention may be synthesized according to the following processes.

The compounds having the above-mentioned formula (I) may be obtained by reacting the compounds having the formula (II) or their salts with the compounds having the general formula (III):

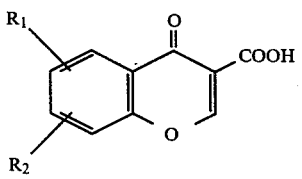

wherein $R_1$ and $R_2$ each represents hydroxy or acyloxy or their reactive derivatives at their carboxyl groups.

In case of using the corresponding free carboxylic acids (—COOH) having the general formula (III) in the said reaction, it is preferable to carry out the reaction in the presence of condensing reagent such as N,N'-dicyclohexylcarbodiimide, N,N'-diethylcarbodiimide, N-cyclohexyl-N'-morpholinoethylcarbodiimide, triethyl phosphite, phosphorus oxychloride, oxalyl chloride, etc.

The representative examples of the reactive derivatives of (III) are acid halides such as acid chloride, acid bromide, etc.; the symmetric acid anhydrides; the mixed anhydrides derived from chlorocarbonate ester, trimethylacetic acid, thioacetic acid, diphenyl acetic acid, etc; the reactive esters with 2-mercaptopyridine, cyanomethanol, p-nitrophenol, 2,4-dinitrophenol, pentachlorophenol, etc.; the reactive amides such as N-acylsaccharin, N-acylphthalimide, etc.

The said reaction may be carried out in an inert solvent in the presence or absence of basic or silylating reagent(s) at the temperature range of $-50°$ C.$-50°$ C., preferably $-20°$ C.$-30°$ C.

The inert solvents to be used in this reaction include, for example, acetone, tetrahydrofuran, dimethylacetamide, N,N-dimethylformamide, dioxane, dichloromethane, chloroform, benzene, toluene, ethyl acetate and their mixed solvents.

The basic reagents include for example alkali hydroxides such as sodium hydroxide, potassium hydroxide, etc.; alkali hydrogen carbonates such as potassium hydrogen carbonate, sodium hydrogen carbonate, etc.; amines such as triethylamine, pyridine, N,N-dimethylaniline, N-methylmorpholine, etc.

The silylating reagents include for example N,O-bis(-trimethylsilyl)acetamide, hexamethyldisilazane, trimethylsilylacetamide, etc.

The compounds having the general formula (III) which are the starting materials of the processes of the production of compounds (I) in the present invention may be obtained by oxidizing the corresponding chromone aldehydes by using Jones reagent (see Reagents for Organic Synthesis, Vol. 1, Page 142). In case of the compound having the general formula (III) wherein the substituents are hydroxy groups, the said compound may also be obtained by oxidation, according to the above oxidation method, of the chromone aldehyde which have acyloxy groups in place of hydroxy groups to the chromone carboxylic acid, followed by hydrolysis.

The acid halides of the compounds having the general formula (III) may be obtained by reacting the compounds having the general formula (III) with halogenating reagents such as phosphorus pentachloride, thionyl chloride, etc.

The aforementioned chromone aldehydes may be produced by the conventional procedures such as the method described in Tetrahedron, Vol. 30, page 3553 (1974), etc.

Among the compounds having the general formula (I) of the present invention, the compounds wherein $R_1$ and $R_2$ both represent hydroxy groups may also be obtained by hydrolyzing the compounds wherein $R_1$ and $R_2$ both represent acyloxy groups. In the hydrolysis, these may be used the alkali hydrogen carbonates such as sodium hydrogen carbonate, potassium hydrogen carbonate, etc.

Illustrative of specified compounds of this invention are the following compounds and their sodium salts.

7β-[D-2-(6,7-Diacetoxychromone-3-carboxamido)-2-(4-hydroxyphenyl)acetamido]-3-acetoxymethyl-3-cephem-4-carboxylic acid.

7β-[D-2-(6,7-Dihydroxychromone-3-carboxamido)-2-(4-hydroxyphenylacetamido]-3-acetoxymethyl-3-cephem-4-carboxylic acid.

7β-[D-2-(7,8-Diacetoxychromone-3-carboxamido)-2-(4-hydroxyphenyl)acetamido]-3-acetoxymethyl-3-cephem-4-carboxylic acid.

7β-[D-2-(7,8-Dihydroxychromone-3-carboxamido)-2-(4-hydroxyphenyl)acetamido]-3-acetoxymethyl-3-cephem-4-carboxylic acid.

7β-[D-2-(6,8-Diacetoxychromone-3-carboxamido)-2-(4-hydroxyphenyl)acetamido]-3-acetoxymethyl-3-cephem-4-carboxylic acid.

7β-[D-2-(6,8-Dihydroxychromone-3-carboxamido)-2-(4-hydroxyphenyl)acetamido]-3-acetoxymethyl-3-cephem-4-carboxylic acid.

The compounds of the present invention show excellent antibacterial activities as described hereinafter and they are effective against Gram-negative bacteria as well as Gram-positive bacteria. These compounds are especially effective against *Pseudomonas aeruginosa*.

Also, the compounds of the present invention have low toxicity. The acute toxicity values [$LD_{50}$ (mouse, oral administration)] of, for example, sodium salt of 7β-[D-2-(6,7-dihydroxychromone-3-carboxamido)-2-(4-hydroxyphenyl)acetamido]-3-acetoxymethyl-3-cephem-4-carboxylic acid and sodium salt of 7β-[D-2-(6,7-diacetoxychromone-3-carboxamido]3-acetoxymethyl-3-cephem-4-carboxylic acid were more than 5 g/kg.

In case of using the compounds of the present invention as antibacterial drugs, they may be generally administered in an amount of 2–300 mg/kg/day, preferably 10–100 mg/kg/day. These drugs may be orally administered in the form of powder, granule, tablet, capsule, syrup, etc.; or parenterally administered in the form of injection, suppository, etc.

These formulations may be produced by the conventional way. In case of the productions of power, granule, tablet, capsule, etc., there may be properly used lactose, starch, cane sugar, glucose, crystal cellulose etc. as diluents; starch, calcium salt of carboxymethylcellulose, calcium carbonate, dextrine, etc. as disintegrators; polyvinylalcohol, ethylcellulose, gum arabic, tragacanth, hydroxypropylcellulose etc. as binding agents; calcium stearate, magnesium stearate, talc etc. as lubricants.

In formulating syrup, there may be properly used cane sugar, sorbitol, glucose, fructose, etc. as sweeteners; gum arabic, tragacanth, sodium salt of carboxymethylcellulose, methylcellulose, sodium alginate, etc. as dispersants and thickeners.

Injection may be produced by using the isotonic agents such as glucose, sodium chloride, sorbitol, etc. and, if necessary, suspending agents, surfactants, pH controlling agents, etc. This injection may be the powder formulation which can be dissolved before administration.

Suppository may be produced by using the base materials such as cacao butter, polyethyleneglycol, Witepsol (the registered trade mark, Dinamite-Novel-AG), etc., and, if necessary, the suppository may be produced by adding the surfactants to these base materials.

The following experiments and examples illustrate this invention, but are not to be construed as limiting the scope thereof.

EXPERIMENT 1

Preparation of chromone-3-carboxylic acids which are the intermediates of the compounds of this invention.

(A) 6,7-Diacetoxychromone-3-carboxylic acid 6,7-Diacetoxychromone-3-carboxyaldehyde (17.8 g) was dissolved in 1 liter of acetone. To this solution was added with stirring Jones reagent (32.8 ml) which had been previously prepared by dissolving chromic acid (133.6 g) in concentrated sulfuric acid (115 ml) diluted with water to a volume of 500 ml.

The reaction mixture was concentrated to 100 ml, and poured into water (900 ml). The precipitates (6.5 g) were collected by filtration, and recrystallized from ethyl acetate to obtain the desired compound (5.9 g).

(B) 6,7-Dihydroxychromone-3-carboxylic acid

To 6,7-diacetoxychromone-3-carboxylic acid (15.3 g) produced in (A) were added acetic acid (300 ml) and concentrated hydrochloric acid (100 ml), and the mixture was stirred for 20 minutes at about 70° C., then cooled.

The precipitates were collected by filtration, and recrystallized from dimethylformamide-water to obtain the desired compound (8.9 g).

7,8-Diacetoxychromone-3-carboxylic acid and 7,8-dihydroxychromone-3-carboxylic acid were prepared by the processes according to (A) and (B), respectively. The properties of the resulting compounds are shown in Table 1.

TABLE 1

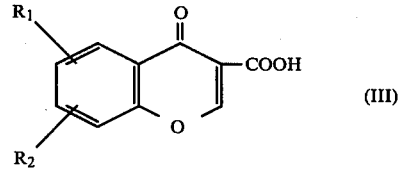

(III)

| No. | (III) 6-position | $R_1$ 7-position | $R_2$ 8-position | IR Spectrum ($cm^{-1}$, nujol) | Molecular Formula Melting point (°C.) | Elemental Analysis (%) Calculated: Found: C | H |
|---|---|---|---|---|---|---|---|
| 1 | HO— | HO— | H | 3370, 3300, 1730, 1635, 1620 | $C_{10}H_6O_6$ >300 | 54.06 54.05 | 2.72 2.60 |
| 2 | $CH_3COO$— | $CH_3COO$— | H | 1780, 1760, 1730, 1620 | $C_{14}H_{10}O_8$ 186–188 | 54.91 54.95 | 3.29 3.08 |
| 3 | H | HO— | HO— | 3380, 3275, 1725, 1620 | $C_{10}H_6O_6$ 265–270* | 54.06 53.65 | 2.72 2.53 |
| 4 | H | $CH_3COO$— | $CH_3COO$— | 1780, 1760, 1740, 1625 | $C_{14}H_{10}O_8$ 178–179 | 54.91 54.90 | 3.29 3.25 |

*decomposition

EXAMPLE 1

7β-[D-2-(6,7-Dihydroxychromone-3-carboxamido)-2-(4-hydroxyphenyl)acetamido]-3-acetoxymethyl-3-cephem-4-carboxylic acid and its sodium salt (a) 6,7-Dihydroxychromone-3-carbonyl chloride A mixture of 6,7-dihydroxychromone-3-carboxylic acid (888 mg, 4 mmol) and thionyl chloride (25 ml) was refluxed for one hour and the thionyl chloride was evaporated. After the addition of benzene, the mixture was evaporated again to dryness and the residue was triturated with dichloromethane to give the desired compound (719 mg).

IR spectrum (cm$^{-1}$, nujol):
1780, 1765, 1645, 1625

(b) 7β-[D-2-(6,7-Dihydroxychromone-3-carboxamido)-2-(4-hydroxyphenyl)acetamido]-3-acetoxymethyl-3-cephem-4-carboxylic acid N,O-Bis(trimethylsilyl)acetamide (742 μl) was added to a stirred suspension of 7β-[D-2-amino-2-(4-hydroxyphenyl)acetamido]-3-acetoxymethyl-3-cephem-4-carboxylic acid (238 mg) in ethyl acetate (10 ml) at 0° C. The mixture was stirred for 20 minutes at 0° C., to which was added the acid chloride (120 mg) described in (a). After stirring for 4 hours at room temperature, the reaction mixture was diluted with ethyl acetate, washed successively with water and saturated brine, and dried (MgSO$_4$) and the solvent was evaporated.

Acetone was added to the residue and the mixture was allowed to stand at room temperature overnight. After removal of acetone, the residue was triturated with ethyl ether to afford the desired compound (101 mg).

Melting point: about 250° C. (decomposition)
Elemental analysis: for C$_{32}$H$_{23}$N$_3$O$_{12}$S

|  | C | H | N |
|---|---|---|---|
| Calculated (%): | 57.06 | 3.44 | 6.24 |
| Found (%): | 51.84 | 3.96 | 5.76 |

IR spectrum (cm$^{-1}$, nujol):
1785, 1730, 1715, 1660, 1630, 1610

NMR spectrum (δ, DMSO-d$_6$):
2.04 (3H, s), 3.40 (1H, d, J=18Hz), 3.58 (1H, d, J=18 Hz), 4.67 (1H, d, J=13 Hz), 4.99 (1H, d, J=13 Hz), 5.05 (1H, d, J=5 Hz), 5.64–5.88 (2H, m), 6.74 (2H, d, J=8.5 Hz), 7.00 (1H, s), 7.27 (2H, d, J=8.5 Hz), 7.44 (1H, s), 8.88 (1H, s), 9.36 (1H, d, J=8 Hz), 10.28 (1H, d, J=8 Hz)

(c) Sodium salt of the compound described in (b)

Sodium 2-ethylhexanoate (0.5 M solution in ethyl acetate, 0.24 ml) was added to a solution of the compound (80 mg) in acetone-N,N-dimethylformamide (2:1, 3 ml). To the mixture was added ethyl acetate-ethyl ether (1:1, 10 ml).

The precipitate formed was filtered off, washed with ethyl acetate-ethyl ether (1:1) and dried to afford the desired compound (67 mg).

Melting point: about 235° C. (decomposition)
Elemental analysis: for C$_{32}$H$_{22}$N$_3$NaO$_{12}$S

|  | C | H | N |
|---|---|---|---|
| Calculated (%): | 55.25 | 3.19 | 6.04 |
| Found (%): | 50.03 | 4.06 | 7.04 |

IR spectrum (cm$^{-1}$, nujol): 1730–1780, 1660, 1600–1630

NMR spectrum (δ, DMSO-d$_6$-D$_2$O):
2.04 (3H, s), 3.16 (1H, d, J=18 Hz), 3.48 (1H, d, J=18 Hz), 4.74 (1H, d, J=13 Hz), 4.90 (1H, d, J=13 Hz), 4.91 (1H, d, J=5 Hz), 5.60 (1H, d, J=5 Hz), 5.64 (1H, s), 6.80 (2H, d, J=8.5 Hz), 7.03 (1H, s), 7.31 (2H, d, J=8.5 Hz), 7.44 (1H, s), 8.83 (1H, s)

EXAMPLE 2

7β-[D-2-(6,7-Diacetoxychromone-3-carboxamido)-2-(4-hydroxyphenyl)acetamido]-3-acetoxymethyl-3-cephem-4-carboxylic acid and its sodium salt (a) 6,7-Diacetoxychromone-3-carbonyl chloride A mixture of 6,7-diacetoxychromone-3-carboxylic acid (18.4 g, 60 mmol), benzene (450 ml), thionyl chloride (8.6 g, 72 mmol) and N,N-dimethylformamide (3 ml) was refluxed for one hour and cooled to room temperature. After the addition of n-hexane (300 ml), the resulting precipitate was filtered off to give the desired compound (17.6 g).

IR spectrum (cm$^{-1}$, nujol): 1780, 1755, 1660, 1625

(b) 7β-[D-2-(6,7-Diacetoxychromone-3-carboxamido)-2-(4-hydroxyphenyl)acetamido]-3-acetoxymethyl-3-cephem-4-carboxylic acid N,O-Bis(trimethylsilyl)acetamide (1 M solution in dichloromethane, 5 ml) was added to a stirred suspension of 7β-[D-2-amino-(6,7-diacetoxychromone-3-carboxamido)-2-(4-hydroxyphenyl)acetamido]-3-acetoxymethyl-3-cephem-4-carboxylic acid (475 mg) in ethyl acetate (5 ml) at 0° C. The mixture was stirred for 20 minutes at 0° C., to which was added a solution of the acid chloride (325 mg) described in (a) in dichloromethane (5 ml). After stirring for 4 hours at 0° C., the reaction mixture was diluted with ethyl acetate, washed successively with water, 0.5 N hydrochloric acid, water and saturated brine, and dried (MgSO$_4$). The solvent was evaporated and the residue was triturated with ethyl ether-n-hexane (2:1) to afford the desired compound (526 mg).

Melting point: 210°–220° C. (decomposition)
Elemental analysis: for C$_{32}$H$_{27}$N$_3$O$_{14}$S

|  | C | H | N |
|---|---|---|---|
| Calculated (%): | 54.16 | 3.84 | 5.92 |
| Found (%): | 52.54 | 3.83 | 5.69 |

IR spectrum (cm$^{-1}$, nujol): 1760–1790, 1735, 1665, 1620

NMR spectrum (δ, DMSO-d$_6$):
2.04 (3H, s), 2.36 (3H, s), 2.37 (3H, s), 3.41 (1H, d, J=18 Hz), 3.57 (1H, d, J=18 Hz), 4.67 (1H, d, J=13 Hz), 4.98 (1H, d, J=13 Hz), 5.05 (1H, d, J=5 Hz), 5.6–5.9 (2H, m), 6.75 (2H, d, J=9 Hz), 7.28 (2H, d, J=9 Hz), 7.88 (1H, s), 8.07 (1H, s), 9.05 (1H, s), 9.40 (1H, d, J=8 Hz), 10.00 (1H, d, J=8 Hz)

(c) Sodium salt of the compound described in (b)

According to the method described in Example 1-c), the desired compound (379 mg) was obtained from the compound (497 mg) described in (b).

Melting point: about 230° C. (decomposition)
Elemental analysis: for C$_{32}$H$_{26}$N$_3$NaO$_{14}$S

|  | C | H | N |
|---|---|---|---|
| Calculated (%): | 52.53 | 3.58 | 5.74 |

|  | C | H | N |
|---|---|---|---|
| Found (%): | 49.85 | 4.11 | 5.54 |

IR spectrum (cm$^{-1}$, nujol):
1720–1780, 1665, 1610

EXAMPLE 3

7β-[D-2-(6,7-Dihydroxychromone-3-carboxamido)-2-(4-hydroxyphenyl)acetaido]-3-acetoxymethyl-3-cephem-4-carboxylic acid Sodium hydrogen carbonate (1 N solution in water, 546 μl) was added to a solution of the compound (200 mg) described in Example 2b) in water (15.45 ml). The mixture was allowed to stand at room temperature overnight, adjusted to pH 2.0 with 1 N hydrochloric acid and extracted with ethyl acetate. The organic layer was washed successively with water and saturated brine, dried (MgSO$_4$) and evaporated. The residue was purified by thin layer chromatography on silica gel to afford the desired compound (108 mg). This compound was identical with the compound described in Example 1b) in all respects [NMR, IR, and thin layer chromatography (silica gel, Merck 5715, benzene/dioxane/acetic acid=4:1:1)].

EXAMPLE 4

7β-[D-2-(7,8-Dihyroxychromone-3-carboxamido)-2-(4-hydroxyphenyl)acetamido]-3-acetoxymethyl-3-cephem-4-carboxylic acid and its sodium salt (a) 7,8-Dihydroxychromone-3-carbonyl chloride A mixture of 7,8-dihydroxychromone-3-carboxylic acid (6.6 g, 30 mmol) and thionyl chloride (25 ml) was refluxed for 1 hour, and the thionyl chloride was removed. After the addition of benzene to the residue, the mixture was evaporated to dryness and the residue was triturated with n-hexane to give the desired compound (7.2 g).

IR spectrum (cm$^{-1}$, nujol): 1775, 1660, 1620

(b) 7β-[D-2-(7,8-Dihydroxychromone-3-carboxamido)-2-(4-hydroxyphenyl)acetamido]-3-acetoxymethyl-3-cephem-4-carboxylic acid N,O-Bis(trimethylsilyl)acetamide (17.3 ml) was added dropwise to a stirred suspension of 7β-[D-2-amino-2-(4-hydroxyphenyl)acetamido]-3-acetoxymethyl-3-cephem-4-carboxylic acid (4.8 g) in ethyl acetate (200 ml) at 2° C. The mixture was stirred for 2 hours at room temperature and cooled to 2° C., to which was added the acid chloride (2.4 g) described in (a). After stirring for 4 hours at 2° C., the reaction mixture was poured into an ice-cooled 0.5 N hydrochloric acid (800 ml) and the mixture was stirred for 30 minutes in an ice bath. The precipitate formed was filtered off, washed with water and dried to afford a crude product (6.5 g). A portion of the product (5.6 g) was stirred in methanol (200 ml) for 2 hours at room temperature and the mixture was filtered. The filtrate was concentrated to a volume of 30 ml and the crystals formed were filtered off, washed successively with methanol and ethyl ether to afford the desired compound (1.2 g).

Melting point: 220°–250° C. (decomposition)
Elemental analysis: for C$_{28}$H$_{23}$N$_3$O$_{12}$S

|  | C | H | N |
|---|---|---|---|
| Calculated (%): | 53.76 | 3.71 | 6.72 |
| Found (%): | 50.34 | 3.78 | 6.34 |

IR spectrum (cm$^{-1}$, nujol): 3250, 1770, 1720, 1665, 1615

NMR spectrum (δ, DMSO-d$_6$):
2.04 (3H, s), 3.48 (2H, m), 4.68 (1H, d, J=14 Hz), 5.00 (1H, d, J=14 Hz), 5.04 (1H, d, J=5 Hz), 5.76 (2H, m), 6.75 (2H, d, J=8 Hz), 7.06 (1H, d, J=8.5 Hz), 7.28 (2H, d, J=8 Hz), 7.56 (1H, d, J=8.5 Hz), 8.94 (1H, s), 9.38 (1H, d, J=8 Hz), 10.24 (1H, d, J=8 Hz)

(c) Sodium salt of the compound described in (b)

According to the method described in Example 1-c), the desired compound (623 mg) was obtained from the compound (626 mg) described in (b).

Melting point: 210°–230° C. (decomposition)
Elemental analysis: for C$_{28}$H$_{22}$N$_3$NaO$_{12}$S

|  | C | H | N |
|---|---|---|---|
| Calculated (%): | 51.93 | 3.42 | 6.49 |
| Found (%): | 49.46 | 3.88 | 6.67 |

IR spectrum (cm$^{-1}$, nujol): 3250, 1770, 1670, 1620

NMR spectrum (δ, DMSO-d$_6$):
2.02 (3H, s), 3.24 (1H, d, J=18 Hz), 3.44 (1H, d, J=18 Hz), 4.80 (1H, d, J=12 Hz) 4.94 (1H, d, J=4.5 Hz), 5.04 (1H, d, J=12 Hz), 5.68 (2H, m), 6.76 (2H, d, J=8 Hz), 7.00 (1H, d, J=8.5 Hz), 7.28 (2H, d, J=8 Hz), 7.46 (1H, d, J=8.5 Hz), 8.88 (1H, s), 9.02 (4H, bs), 10.36 (1H, d, J=8 Hz)

EXAMPLE 5

7β-[D-2-(7,8-Diacetoxychromone-3-carboxamido)-2-(4-hydroxyphenyl)acetamido]-3-acetoxymethyl-3-cephem-4-carboxylic acid (a) 7,8-Diacetoxychromone-3-carbonyl chloride A mixture of 7,8-diacetoxychromone-3-carboxylic acid (9.5 g, 31 mmol), thionyl chloride (2.6 ml), N,N-dimethylformamide (0.1 ml) and benzene (300 ml) was refluxed for 1.5 hours. After the addition of thionyl chloride (2.6 ml) and N,N-dimethylformamide (0.1 ml), the mixture was refluxed for a further hour and evaporated to dryness. The residue was triturated with n-hexane to afford the desired compound (9.3 g, 92.6%).

IR spectrum (cm$^{-1}$, nujol): 1780, 1770, 1670, 1620

(b) 7β-[D-2-(7,8-Diacetoxychromone-3-carboxamido)-2-(4-hydroxyphenyl)acetamido]-3-acetoxymethyl-3-cephem-4-carboxylic acid N,O-Bis(trimethylsilyl)acetamide (1.23 ml) was added dropwise to a suspension of 7β-[D-2-amino-2-(4-hydroxyphenyl)acetamido]-3-acetoxymethyl-3-cephem-4-carboxylic acid (211 mg) in ethyl acetate (5 ml) at 0° C. The mixture was stirred for 1 hour at 0° C., to which was added the acid chloride (162 mg) described in (a). After stirring for 4 hours at 0° C., the reaction mixture was diluted with ethyl acetate (150 ml), washed successively with water, 0.5 N hydrochloric acid, water and saturated brine and dried (MgSO$_4$). The solvent was evaporated and acetone (10 ml) was added to the residue. The mixture was stirred for 4 hours at room temperature, concentrated to a volume of ca. 5 ml and purified by thin layer chromatography on silica gel to afford the desired compound (24 mg).

Melting point: 200°–210° C. (decomposition) Elemental analysis: for $C_{32}H_{27}N_3O_{14}S$

|  | C | H | N |
|---|---|---|---|
| Calculated (%): | 54.16 | 3.84 | 5.92 |
| Found (%): | 50.34 | 3.75 | 6.34 |

IR spectrum (cm$^{-1}$, nujol): 1785, 1775, 1770, 1740, 1710, 1675, 1655, 1630, 1610, 1600

NMR spectrum ($\delta$, DMSO-d$_6$):

2.04 (3H, s), 2.39 (3H, s), 2.45 (3H, s), 3.48 (2H, m), 4.68 (1H, d, J=13 Hz), 4.96 (1H, d, J=13 Hz), 5.04 (1H, d, J=5 Hz), 5.72 (1H, d, J=8 Hz), 5.76 (1H, m), 6.74 (2H, d, J=8.5 Hz), 7.26 (2H, d, J=8.5 Hz), 7.58 (1H, d, J=9 Hz), 8.14 (1H, d, J=9 Hz), 9.00 (1H, s), 9.40 (1H, d, J=8 Hz), 9.46 (1H, s), 9.97 (1H, d, J=8 Hz)

The compounds obtained in these examples were tested for their antibacterial activities in vitro.

METHOD

Minimal inhibitory concentration (MIC) was determined by the standard agar dilution method of the Japan Society of Chemotherapy.

The compounds described in Examples 1, 2 and 4 were dissolved in sterilized water; the compound described in Example 5 was dissolved in acetone-water (1:1); and the control compound, cephaloglycin, was dissolved in a 3% sodium hydrogen carbonate solution.

Serial two-fold dilutions were made from the above solutions.

One-ml aliquots of each dilution were mixed with 9 ml of Mueller Hinton agar in petri-dishes to make agar plates containing the compound at serially diluted concentrations. After agar hardened, plates were put in an incubator at 37° C. for 1.5–2 hours with the lids slightly open to evaporate acetone off the plates.

Test organisms were grown for 18 hours at 37° C. in Trypticase Soy broth and diluted in saline to approximately 10$^6$ colony forming units per ml. A loopful of each cell suspension was applied on the agar plate mentioned above and the plates were incubated for 18 hours at 37° C. before MIC was determined.

MIC values of the compounds described in Examples 1, 2 and 4 were determined as their sodium salts and the compound described in Example 5 was determined as a free carboxylic acid.

The results are shown in Table 2.

| -continued | |
|---|---|
| acid | |
| crystalline cellulose | 250 mg |
| calcium salt of carboxy- | 80 mg |
| methylcellulose | 38 mg |
| calcium stearate | 2 mg |
| 1 tablet | 370 mg |

The tablet was produced by usual method with the above formulation.

What is claimed is:

1. A cephalosporin derivative of the formula

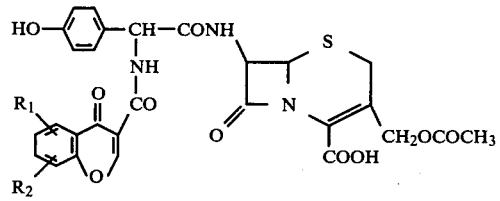

wherein R$_1$ and R$_2$ each represents hydroxyl, acetoxy, propionyloxy or benzoyloxy or a pharmaceutically acceptable salt thereof.

2. A compound as claimed in claim 10 wherein R$_1$ and R$_2$ occupy 6 and 7 positions or 7 and 8 positions.

3. A compound as claimed in claim 2 wherein said compound is 7$\beta$-[D-2-(6,7-dihydroxychromone-3-carboxamido)-2-(4-hydroxyphenyl)acetamido]-3-acetoxymethyl-3-cephem-4-carboxylic acid or pharmaceutically acceptable salt thereof.

4. A compound as claimed in claim 2 wherein said compound is 7$\beta$-[D-2-(6,7-diacetoxychromone-3-carboxamido)-2-(4-hydroxyphenyl)acetamido]-3-acetoxymethyl-3-cephem-4-carboxylic acid or pharmaceuticaly acceptable salt thereof.

5. A compound as claimed in claim 2 wherein said compound is 7$\beta$-[D-2-(7,8-dihydroxychromone-3-carboxamido)-2-(4-hydroxyphenyl)acetamido]-3-acetoxymethyl-3-cephem-4-carboxylic acid or pharmaceutically acceptable salt thereof.

6. A compound as claimed in claim 2 wherein said compound is 7$\beta$-[D-2-(7,8-diacetoxychromone-3-carboxamido)-2-(4-hydroxyphenyl)acetoamido]-3-acetoxymethyl-3-cephem-4-carboxylic acid or pharmaceutically acceptable salt thereof.

TABLE 2

| Test compound | | Test bacteria | MIC ($\mu$g/ml) | | | | | |
|---|---|---|---|---|---|---|---|---|
| | | | Staphylococcus aureus 209P | Escherichia coli NIHJ | Klebsiella pneumoniae EK-6 | Proteus morganii EP-14 | Pseudomonas aeruginosa EP-172 | Serratia marcescens ES-75 |
| Example | 1 | | 3.13 | 3.13 | 0.2 | 50 | 3.13 | 3.13 |
| | 2 | | 6.25 | 12.5 | 0.2 | 100 | 3.13 | 6.25 |
| | 4 | | 0.8 | 12.5 | 0.2 | 100 | 1.56 | 100 |
| | 5 | | 6.25 | 3.13 | 0.4 | 25 | 3.13 | 25 |
| Cephaloglycin | | | 0.8 | 3.13 | 1.56 | 25 | 100 | 100 |

EXAMPLE 6

Formulation for tablet

7$\beta$-[D-2-(6,7-Dihydroxychromone-3-carboxamido)-2-(4-hydroxyphenyl)acetamido]-3-acetoxymethyl-3-cephem-4-carboxylic 7. An antibacterial composition comprising an antibacterially effective amount of (a) a compound of the formula

11

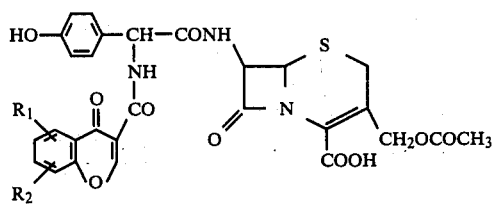

wherein $R_1$ and $R_2$ each represents hydroxy, acetoxy, propionylxy or benzoyloxy or (b) a pharmaceutically acceptable salt thereof and a pharmaceutically acceptable carrier therefor.

* * * * *

12

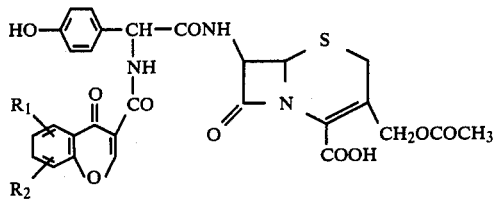

wherein $R_1$ and $R_2$ each represents hydroxy, acetoxy, propionylxy or benzoyloxy or (b) a pharmaceutically acceptable salt thereof and a pharmaceutically acceptable carrier therefor.

* * * * *